(12) United States Patent
Tsukagoshi et al.

(10) Patent No.: US 9,277,893 B2
(45) Date of Patent: Mar. 8, 2016

(54) X-RAY COMPUTED TOMOGRAPHY APPARATUS

(75) Inventors: Shinsuke Tsukagoshi, Nasushiobara (JP); Masaharu Tsuyuki, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/973,192

(22) Filed: Dec. 20, 2010

(65) Prior Publication Data

US 2011/0158380 A1 Jun. 30, 2011

(30) Foreign Application Priority Data

Dec. 24, 2009 (JP) ................... 2009-293358

(51) Int. Cl.
*A61B 6/03* (2006.01)
*A61B 6/02* (2006.01)
*A61B 6/00* (2006.01)
*G06T 7/00* (2006.01)
*G06T 11/00* (2006.01)
(Continued)

(52) U.S. Cl.
CPC .............. *A61B 6/032* (2013.01); *A61B 6/022* (2013.01); *A61B 6/487* (2013.01); *G06T 7/0075* (2013.01); *G06T 11/006* (2013.01); *H04N 5/32* (2013.01); *H04N 13/021* (2013.01); *H04N 13/0253* (2013.01); *G06T 2207/10121* (2013.01); *G06T 2207/30096* (2013.01); *G06T 2207/30101* (2013.01); *G06T 2211/436* (2013.01)

(58) Field of Classification Search
CPC ......... A61B 6/022; A61B 6/032; A61B 6/035
USPC ............... 378/4, 41, 15, 17, 42, 196, 197
See application file for complete search history.

(56) References Cited

U.S. PATENT DOCUMENTS

| 4,214,267 A | 7/1980 | Roese et al. |
| 4,578,802 A * | 3/1986 | Itoh .............................. 378/41 |
| 4,637,040 A * | 1/1987 | Sohval et al. ................... 378/9 |

(Continued)

FOREIGN PATENT DOCUMENTS

| JP | 03-123537 A | 5/1991 |
| JP | 04-259454 A | 9/1992 |

(Continued)

OTHER PUBLICATIONS

Office Action issued Jun. 2, 2015 in Japanese Patent Application No. 2014-167865.

(Continued)

*Primary Examiner* — Allen C. Ho
(74) *Attorney, Agent, or Firm* — Oblon, McClelland, Maier & Neustadt, L.L.P.

(57) ABSTRACT

In one embodiment, an X-ray computed tomography apparatus includes an X-ray tube, an X-ray detector, a rotating mechanism, a high voltage generating unit, a reconstruction processing unit, a projection image generating unit configured to generate a projection image based on output from the X-ray detector, an image display unit, and a fluoroscopy control unit configured to control the rotating mechanism, the high voltage generating unit, the X-ray detector, the projection image generating unit and the image display unit to implement stereo fluoroscopy.

15 Claims, 9 Drawing Sheets

(51) Int. Cl.
 *H04N 5/32* (2006.01)
 *H04N 13/02* (2006.01)

(56) References Cited

U.S. PATENT DOCUMENTS

| | | | | |
|---|---|---|---|---|
| 4,737,972 A * | 4/1988 | Schoolman | | 378/41 |
| 5,073,914 A * | 12/1991 | Asahina et al. | | 378/42 |
| 5,090,038 A * | 2/1992 | Asahina | | 378/41 |
| 5,163,076 A * | 11/1992 | Koyama | | 378/42 |
| 5,173,852 A * | 12/1992 | Lonn | | 378/9 |
| 5,233,639 A * | 8/1993 | Marks | | 378/42 |
| 5,361,291 A * | 11/1994 | Toth et al. | | 378/12 |
| 5,448,610 A * | 9/1995 | Yamamoto et al. | | 378/19 |
| 5,568,533 A * | 10/1996 | Kumazaki et al. | | 378/156 |
| 6,041,097 A * | 3/2000 | Roos et al. | | 378/62 |
| 6,256,372 B1 | 7/2001 | Aufrichtig et al. | | 378/41 |
| 6,359,961 B1 | 3/2002 | Aufrichtig et al. | | 378/41 |
| 6,393,090 B1 | 5/2002 | Hsieh et al. | | 378/4 |
| 6,400,791 B1 | 6/2002 | Schwarz | | 378/17 |
| 6,449,333 B1 * | 9/2002 | Yamasaki | | 378/42 |
| 6,580,777 B1 * | 6/2003 | Ueki et al. | | 378/17 |
| 6,760,469 B1 | 7/2004 | Berestov et al. | | 382/132 |
| 6,807,292 B1 * | 10/2004 | Goto et al. | | 382/128 |
| 6,862,364 B1 | 3/2005 | Berestov | | 382/132 |
| 6,914,959 B2 * | 7/2005 | Bailey et al. | | 378/65 |
| 7,031,425 B2 * | 4/2006 | Hsieh et al. | | 378/5 |
| 7,035,371 B2 * | 4/2006 | Boese et al. | | 378/41 |
| 7,164,745 B2 | 1/2007 | Tsuyuki | | |
| 7,209,538 B2 * | 4/2007 | Sukovic et al. | | 378/42 |
| 7,227,925 B1 * | 6/2007 | Mansfield et al. | | 378/65 |
| 7,486,763 B2 * | 2/2009 | Popescu | | 378/15 |
| 7,558,368 B2 * | 7/2009 | Klingenbeck-Regn | | 378/41 |
| 7,657,304 B2 * | 2/2010 | Mansfield et al. | | 600/427 |
| 7,684,538 B2 * | 3/2010 | Morton et al. | | 378/10 |
| 7,693,256 B2 * | 4/2010 | Brahme et al. | | 378/41 |
| 7,702,065 B2 * | 4/2010 | Lozano Fantoba et al. | | 378/41 |
| 7,708,462 B2 * | 5/2010 | Fujiwara et al. | | 378/207 |
| 7,809,102 B2 * | 10/2010 | Brada et al. | | 378/20 |
| 7,826,585 B2 * | 11/2010 | Proksa et al. | | 378/9 |
| 7,869,561 B2 * | 1/2011 | Dafni | | 378/9 |
| 7,933,378 B2 * | 4/2011 | Proksa | | 378/9 |
| 7,949,089 B2 * | 5/2011 | Dafni et al. | | 378/9 |
| 8,094,778 B2 * | 1/2012 | Sendai | | 378/41 |
| 8,160,337 B2 * | 4/2012 | Rasche et al. | | 382/131 |
| 8,180,017 B2 * | 5/2012 | Forthmann et al. | | 378/9 |
| 8,270,562 B2 * | 9/2012 | Sainath et al. | | 378/9 |
| 8,471,222 B2 * | 6/2013 | Handa et al. | | 250/491.1 |
| 2003/0031291 A1 * | 2/2003 | Yamamoto et al. | | 378/41 |
| 2004/0208279 A1 * | 10/2004 | Xiao et al. | | 378/41 |
| 2005/0047541 A1 * | 3/2005 | Tsuyuki | | 378/4 |
| 2007/0003007 A1 * | 1/2007 | Carrano et al. | | 378/41 |
| 2008/0031411 A1 * | 2/2008 | Klingenbeck-Regn | | 378/41 |
| 2009/0257551 A1 * | 10/2009 | Dafni et al. | | 378/6 |
| 2009/0285355 A1 * | 11/2009 | Brada et al. | | 378/20 |

FOREIGN PATENT DOCUMENTS

| | | |
|---|---|---|
| JP | 2000-83941 | 3/2000 |
| JP | 2003-038477 A | 2/2003 |
| JP | 2006-141709 A | 6/2006 |
| JP | 2006-524529 A | 11/2006 |
| JP | 2007-301228 A | 11/2007 |

OTHER PUBLICATIONS

Office Action mailed Dec. 14, 2015, in Chinese Application No. 201010606070.3.

* cited by examiner

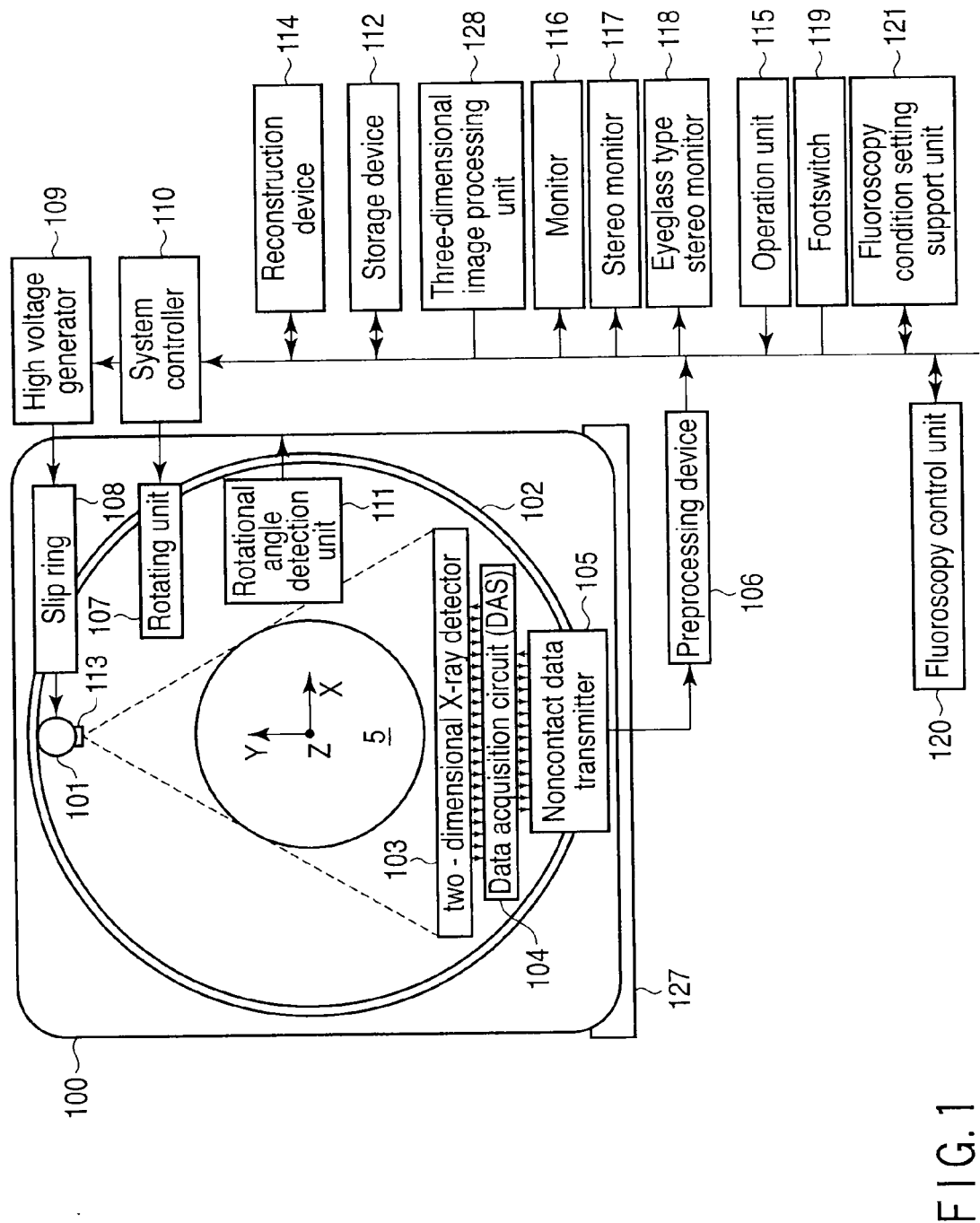
F I G. 1

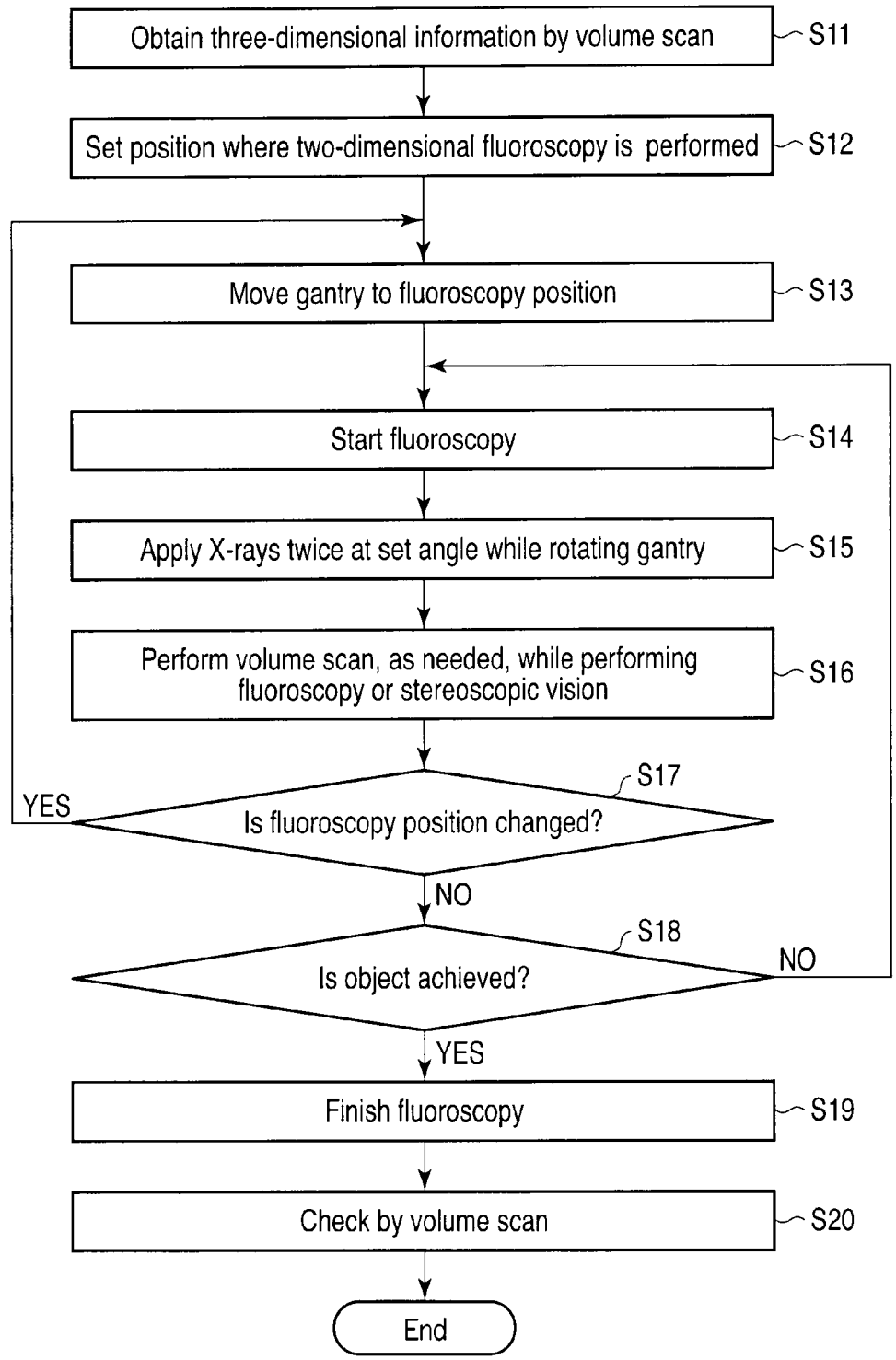
F I G. 3

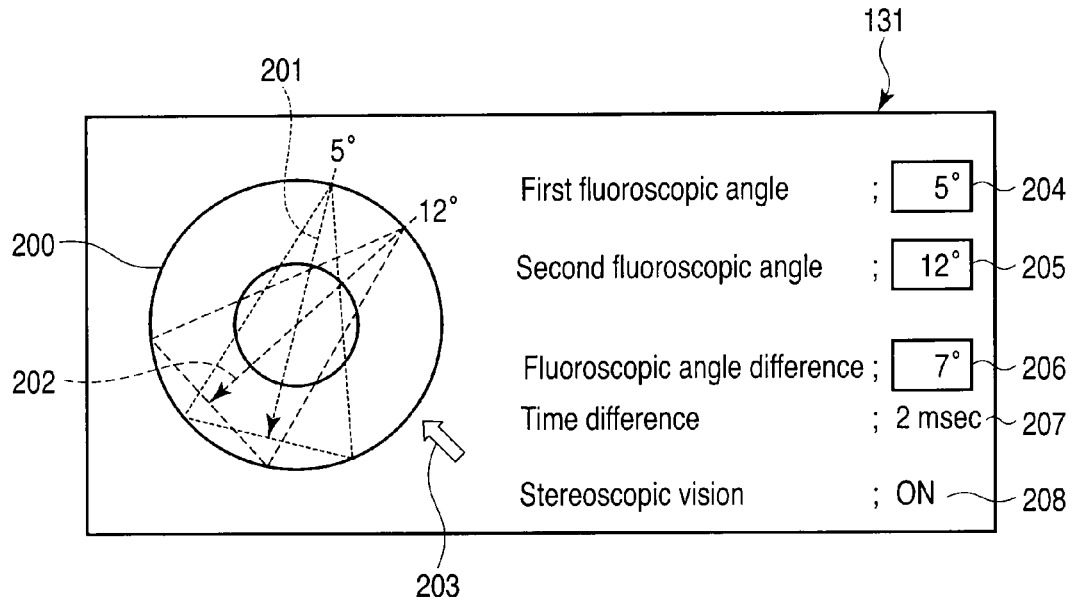
F I G. 4
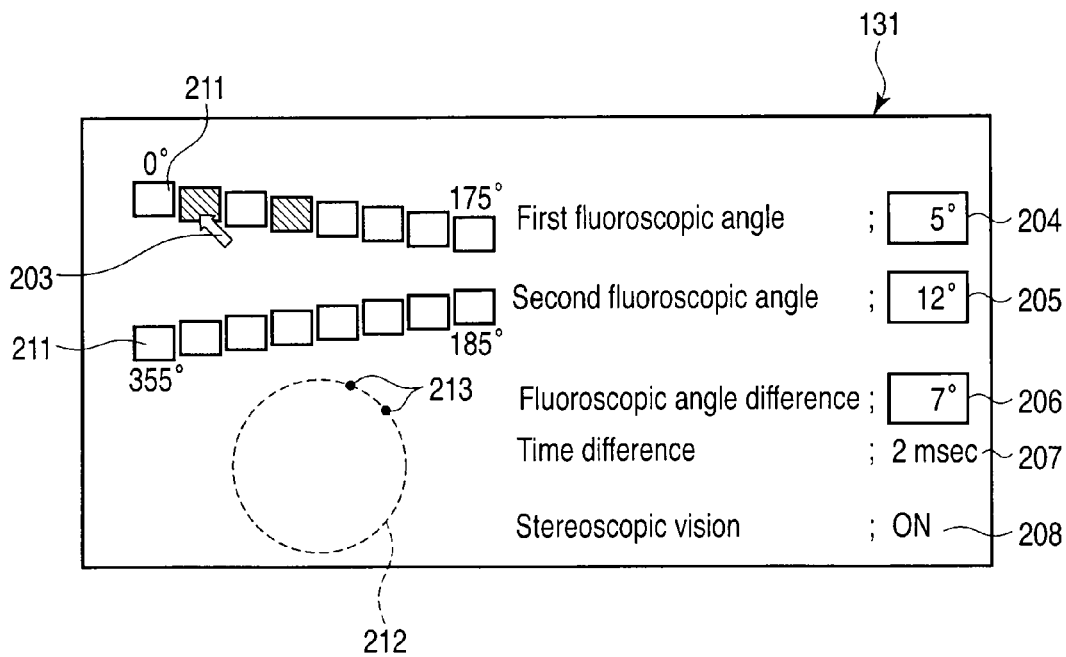
F I G. 5

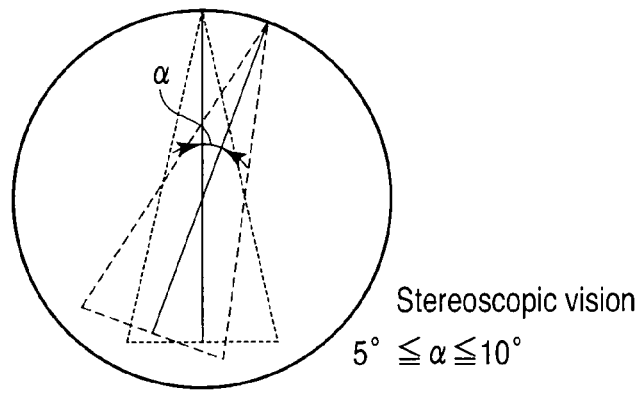
FIG. 10  Stereoscopic vision  $5° \leq \alpha \leq 10°$
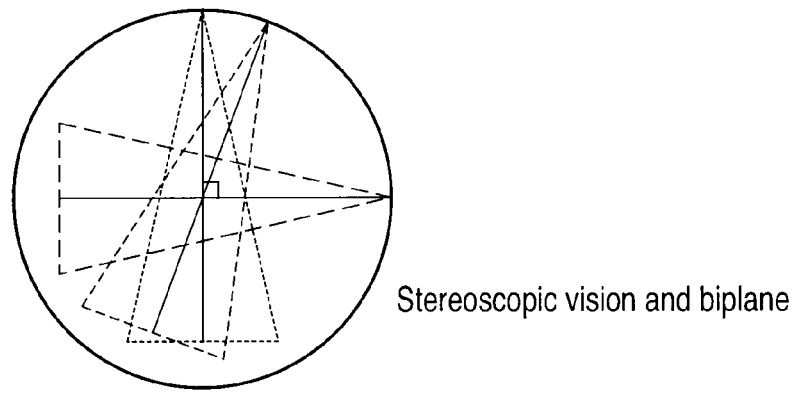
FIG. 11  Stereoscopic vision and biplane
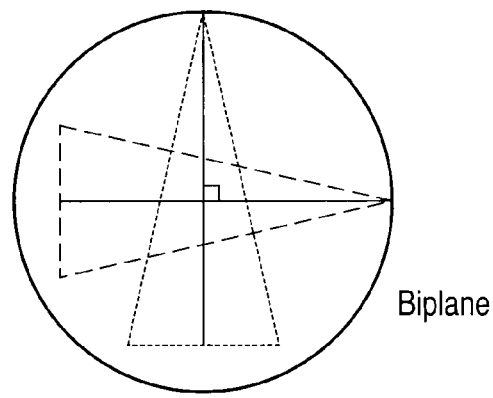
FIG. 12  Biplane

X-RAY COMPUTED TOMOGRAPHY APPARATUS

CROSS-REFERENCE TO RELATED APPLICATIONS

This application is based upon and claims the benefit of priority from Japanese Patent Application No. 2009-293358, filed Dec. 24, 2009; the entire contents of which are incorporated herein by reference.

FIELD

Embodiments described herein relate generally to an X-ray computed tomography apparatus.

BACKGROUND

Recently, an X-ray computed tomography apparatus capable of performing so-called CT fluoroscopy has come on the market. CT fluoroscopy is a technique of reconstruction and displaying tomograms in real time concurrently with a scan. CT fluoroscopy is effective for catheterization. CT reconstruction includes a very large number of processing steps. In current CT fluoroscopy, the field of view in the body axis direction is only about 6 mm (see FIG. 13). It is possible to expand the fluoroscopy range up to, for example, 32 mm by increasing the slice width of each slice. Increasing the slice thickness will make a partial volume phenomenon more noticeable and blur the tip of a needle or catheter. This makes it impossible to use an X-ray computed tomography apparatus for catheterization and the like.

A recent wide area detector includes, for example, 320 arrays (320 segments).

However, the fluoroscopy range that allows CT fluoroscopy is still limited by the reconstruction processing speed. As shown in FIG. 14, CT fluoroscopy does not effectively use many segments.

Currently, therefore, it is not possible to practically apply an X-ray computed tomography apparatus to a situation that requires instantaneousness and a wide field of view as in the case of catheterization and the like. Even if advances in reconstruction techniques will allow to reconstruct several hundred slices in real time, it is necessary to continuously irradiate a wide range with X-rays. This leads to the problem of exposure.

BRIEF DESCRIPTION OF THE DRAWINGS

FIG. 1 is a view showing the arrangement of an X-ray computed tomography apparatus according to an embodiment;

FIG. 3 is a flowchart showing an operation procedure of this embodiment;

FIG. 4 is a view showing an example of a fluoroscopic angle setting window in step S12 in FIG. 3;

FIG. 5 is a view showing another example of the fluoroscopic angle setting window in step S12 in FIG. 3;

FIG. 10 is a view showing a fluoroscopic angle difference α in stereo fluoroscopy in this embodiment;

FIG. 11 is a view showing an example of fluoroscopy positions in stereo fluoroscopy and orthogonal biplane fluoroscopy in this embodiment;

FIG. 12 is a view showing an example of a fluoroscopy position in orthogonal biplane fluoroscopy in this embodiment;

DETAILED DESCRIPTION

In one embodiment, an X-ray computed tomography apparatus includes an X-ray tube; an X-ray detector; a rotating mechanism; a high voltage generating unit; a reconstruction processing unit; a projection image generating unit configured to generate a projection image based on output from the X-ray detector; an image display unit; and a fluoroscopy control unit configured to control the rotating mechanism, the high voltage generating unit, the X-ray detector, the projection image generating unit and the image display unit to implement stereo fluoroscopy.

An embodiment will be described below with reference to the views of the accompanying drawing. Note that X-ray computed tomography apparatuses include various types of apparatuses, e.g., a rotate/rotate-type apparatus in which an X-ray tube and an X-ray detector rotate together around an object, a stationary/rotate-type apparatus in which many detectors are arranged on a ring, and only an X-ray tube rotates around an object, and a stationary/stationary-type apparatus in which a plurality of X-ray tubes are arranged on a ring, and a plurality of X-ray detectors are also arranged on a ring. The present embodiment can be more effectively applied to the rotate/rotate- and stationary/rotate-types. In addition, X-ray computed tomography apparatuses include a single tube type apparatus in which a pair of an X-ray tube and an X-ray detector are mounted on a rotating frame, and a so-called multi-tube type apparatus in which a plurality of pairs of X-ray tubes and X-ray detectors are mounted on a rotating frame. The present embodiment can be applied to either type. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and migration of the electron-hole pairs to an electrode, i.e., a photoconductive phenomenon. As an X-ray detection element, either of these schemes can be used.

Figure 2:
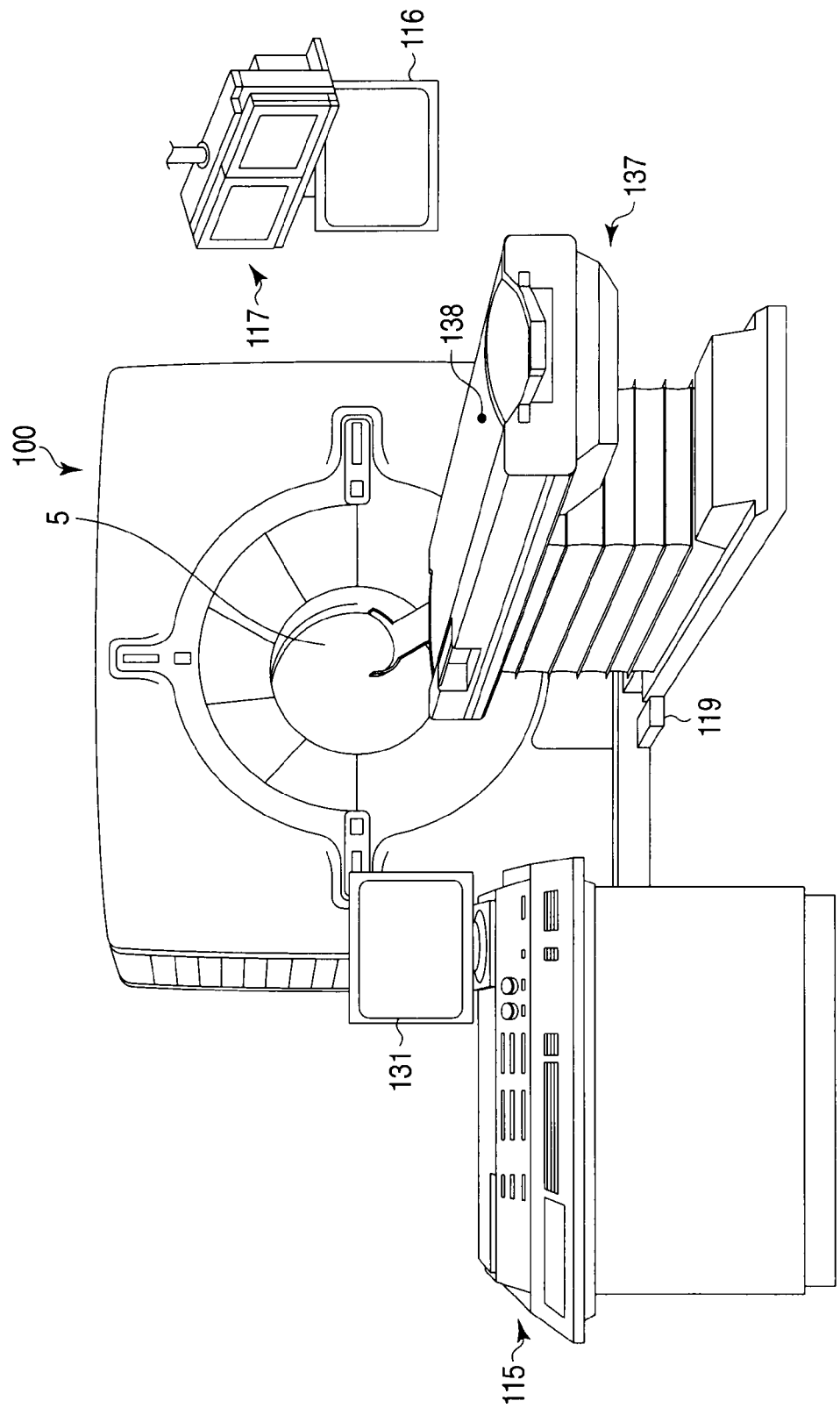
FIG. 2 is a perspective view showing the outer appearance of the X-ray computed tomography apparatus in FIG. 1.

FIG. 1 shows the arrangement of an X-ray computed tomography apparatus according to this embodiment. FIG. 2 shows an outer appearance of the apparatus. A gantry 100 includes an X-ray tube 101 and a two-dimensional X-ray detector 103. A collimator unit 113 is attached to the X-ray irradiation window of the X-ray tube 101. The collimator unit 113 has a structure designed to arbitrarily change the cone angle of X-rays within the range from the maximum cone angle corresponding to the width of the X-ray detector 103 in the Z-axis direction to the minimum cone angle corresponding to one array (one segment) of the X-ray detector 103. The X-ray detector 103 is an area detector (also referred to as a two-dimensional array detector) including, for example, 320 arrays (320 segments) and having a wide field of view in the Z-axis direction.

The X-ray tube 101 and the X-ray detector 103 are mounted on an annular frame 102 supported so as to be rotatable around a rotation axis Z. The X-ray detector 103 faces the X-ray tube 101 through the object placed on a top 138 of a bed 137 in an imaging area 5 formed as an opening in the central portion of the gantry 100. A rotating unit 107 can rotate the annular frame 102 at a high speed of, for example, 0.25 sec/rotation. A rotational angle detection unit 111 implemented by a rotary encoder detects the rotational angle of the annular frame 102. The X-ray tube 101 receives a tube voltage and a filament current from a high voltage generator 109 via a slip ring 108. The high voltage generator 109 may be mounted on the annular frame 102 together with a capacitor. The X-ray tube 101 generates X-rays upon receiving the tube voltage and the filament current. The X-ray detector 103 detects the X-rays transmitted through the object.

The gantry 100 is supported on a tilt mechanism 127 so as to be tiltable. This can tilt the rotation axis Z of the annular frame 102, i.e., the rotation axis Z of the X-ray tube 101 and X-ray detector 103, forward or backward from the horizontal position at an arbitrary angle.

A data acquisition circuit 104 generally called a DAS (Data Acquisition System) converts a signal output from the X-ray detector 103 for each channel into a voltage signal, amplifies it, and further converts it into a digital signal. This data (raw data) is sent to a preprocessing device 106 via a noncontact data transmitter 105. The preprocessing device 106 performs correction processing such as sensitivity correction for the raw data. A storage device 112 then stores the resultant data as so-called projection data at a stage immediately before reconstruction processing. A fluoroscopy control unit 120 reads out projection data from the storage device 112 in an order corresponding to the arrangement of the respective detection elements to generate the two-dimensional distribution of projection data, i.e., a projection image.

The storage device 112 is connected to a system controller 110 via a data/control bus, together with a reconstruction device 114, a three-dimensional image processing unit 128, a monitor 116, a stereo monitor 117, an eyeglass type stereo monitor 118, the operation unit 115, a footswitch 119, a fluoroscopy condition setting support unit 121, and the fluoroscopy control unit 120. The reconstruction device 114 reconstructs volume data based on projection data stored in the storage device 112 by using a cone beam image reconstruction method. As a cone beam image reconstruction method, the Feldkamp method is generally used. The Feldkamp method is an approximate reconstruction method based on a fan beam convolution/back projection method. Convolution processing is performed by regarding data as fan projection data on the premise that the cone angle is relatively small. However, back projection processing is performed along an actual ray corresponding to a tilted cone angle.

The three-dimensional image processing unit 128 generates a two-dimensional image which can be displayed on a two-dimensional window from volume data by volume rendering. Volume rendering is a technique of selectively extracting a target portion by defining opacities and colors stepwise in accordance with pixel values or the like. In practice, the three-dimensional image processing unit 128 sequentially adds the respective pixel values at points on a ray while applying predetermined coefficients to the pixel values, and sets the addition result as a pixel value on a projection plane. Such coefficients are determined based on opacities with respect to pixel values, the distances in the line-of-sight direction (the distances from the projection plane to the corresponding points), shading conditions, and the like. This volume rendering allows to generate a pseudo three-dimensional image like a seen-through image.

As described above, this embodiment includes the monitor 116, the stereo monitor 117, and the eyeglass type stereo monitor 118 as display units. The monitor 116 and the stereo monitor 117 are installed in an imaging room, together with the gantry 100. The operator who is executing, for example, catheterization wears the eyeglass type stereo monitor 118. The monitor 116 displays three-dimensional images and projection images. The stereo monitor 117 and the eyeglass type stereo monitor 118 each include a right-eye monitor unit (or a right-eye display area) and a left-eye monitor unit (or a left-eye display area). The operator uses them in the stereo fluoroscopy mode (to be described later). The operator visually recognizes the right- and left-eye monitor units of the stereo monitor 117 or the eyeglass type stereo monitor 118 with his/her right and left eyes to implement stereoscopic vision. This allows the operator to recognize the stereoscopic structure of the target.

The operation unit 115 is provided to mainly allow the operator to execute switching operation between the general CT scan mode and the fluoroscopy mode and condition setting operation for the respective modes. The general CT scan mode is a mode for executing a general volume scan, and is not a new function. A detailed description of this mode will therefore be omitted. The fluoroscopy mode is a mode for implementing a fluoroscopy function approximate to X-ray fluoroscopy using an X-ray diagnosis apparatus by using the X-ray computed tomography apparatus. The fluoroscopy mode will be described in detail below.

The fluoroscopy condition setting support unit 121 provides a setting window for allowing the operator to easily and simply set fluoroscopy conditions. The provided setting window will be described later. The footswitch 119 is a foot-operated type switch which can be placed at an arbitrary position on the floor near the gantry 100 or the bed 137. In the fluoroscopy mode, while the operator steps on the footswitch 119 to keep it on, this apparatus irradiates the object with X-rays and executes live fluoroscopy. That is, in the fluoroscopy mode, every time the X-ray tube 101 makes one rotation, the apparatus captures two or three images or a more set number of images. When the X-ray tube 101 continuously rotates, the apparatus repeatedly generates images at different imaging angles at a period equal to the time taken for one rotation of the X-ray tube 101, e.g., 0.4 sec. Displaying the repeatedly generated images in real time makes it possible to provide a moving image which allows the operator to recognize at least the dynamic displacement of an object even though the frame rate is relatively low. The fluoroscopy control unit 120 controls the respective units to execute CT fluoroscopy operation.

The fluoroscopy mode includes a stereo fluoroscopy form, a biplane form, and a combined form of the stereo fluoroscopy form and the biplane form. Fluoroscopy is operation to display a series of X-ray images (projection images) repeatedly detected by the X-ray detector 103 as a moving image in real time. Stereo fluoroscopy is operation to display right- and left-eye images, as moving images, which correspond to a binocular parallax falling within the range of 5° to 10°. The operator can stereoscopically view the target by viewing a right-eye image with his/her right eye and a left-eye image with his/her left eye.

These forms differ in fluoroscopic angles. In the fluoroscopy mode according to this embodiment, the X-ray tube 101 and the X-ray detector 103 continuously rotate around the object, together with the frame 102. While they keep rotating and the footswitch 119 is in the ON state, the apparatus repeatedly generates pulse-like X-rays every time the X-ray tube 101 passes through a pair of viewpoints (to be referred to as fluoroscopy positions or fluoroscopic angles hereinafter), of many viewpoints on the rotational orbit of the X-ray tube 101, which corresponds to a binocular parallax. The apparatus generates a projection image (planar image) based on data output from the X-ray detector 103 in synchronism with the generation of the X-rays. The monitors 116, 117, and 118 assigned to the respective fluoroscopy positions in advance then display the projection image as a moving image in real time.

When the stereo fluoroscopy form is selected, the two fluoroscopic angles are limited to an angle difference in the range of 5° to 10°. This angle difference corresponds to a binocular parallax. Viewing two fluoroscopic images with the left and right eyes can implement stereoscopic vision. When the biplane form is selected, the difference between the two fluoroscopic angles is not specifically limited but is typically and initially set to 90°. When the combined form is selected, three fluoroscopy positions are set. The two fluoroscopy positions are set to an angle difference in the range of 5° to 10° to make the apparatus function in the stereo fluoroscopy form. One of the two fluoroscopy positions and the remaining fluoroscopy position are typically set to an angle difference of 90° to make the apparatus function in the biplane form.

FIG. 3 shows an operation procedure in the fluoroscopy mode to be performed under the control of the fluoroscopy control unit 120 according to this embodiment. First of all, the apparatus performs a general CT scan, a volume scan in this case (S11). The reconstruction device 114 reconstructs volume data based on the projection data acquired by the volume scan. The three-dimensional image processing unit 128 generates a pseudo three-dimensional image from the volume data. The fluoroscopy condition setting support unit 121 displays the pseudo three-dimensional image to set a fluoroscopy position (Z position) with respect to the pseudo three-dimensional image (S12). The gantry 100 is moved to the set position.

In addition, this apparatus forms a fluoroscopy condition setting support window including the pseudo three-dimensional image. The fluoroscopy conditions mainly include a condition for the selection of the stereo fluoroscopy form, the biplane form, or the combined form and a condition for the designation of a fluoroscopic angle. The apparatus displays a line representing the rotation axis Z of the X-ray tube 101 upon superimposing it on the pseudo three-dimensional image. A plurality of candidate lines with different fluoroscopic angles are superimposed within a plane which is centered on the above line and perpendicular to it. A candidate line is a line connecting a viewpoint on the rotational orbit from which X-rays are applied to the center of a detector. When the operator designates one of the plurality of candidate lines which is determined as a line allowing to easily see a surgery target region, the apparatus displays a translucent cone beam model indicating the field of view centered on the designated candidate line. The operator confirms that a fluoroscopy target region is included in the cone beam model, and determines the designated candidate line, thus setting a fluoroscopic angle. When the stereo fluoroscopy form is selected, the apparatus displays only candidate lines within the range of angle difference of 5° to 10° from the determined fluoroscopic angle. This indicates that a limitation is practically imposed on the differences between fluoroscopic angles. This angle difference range corresponds to the range of binocular parallaxes which can implement stereoscopic vision (FIG. 10). In the stereo fluoroscopy form, two fluoroscopic angles are set.

Figure 15:
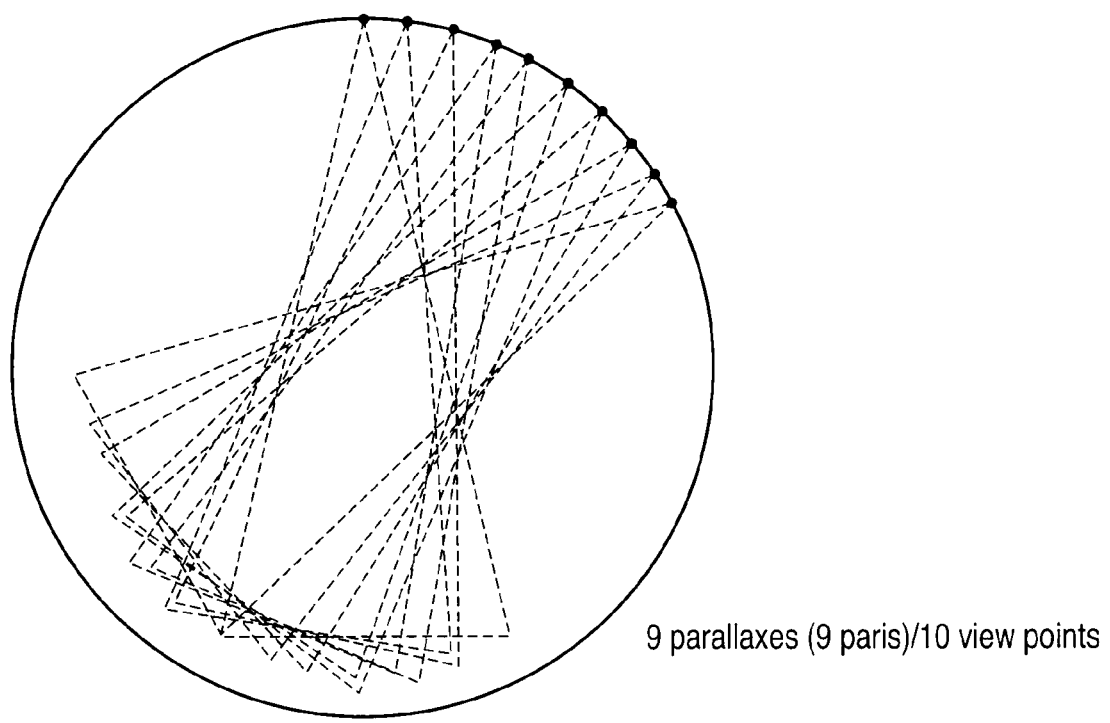
FIG. 15 is a view showing the application of this embodiment to 9 parallaxes/10 view points.

As shown in FIG. 15, it is possible to obtain a fluoroscopic image with three or more viewpoints with consecutive angle differences (parallaxes). An adjacent pair of fluoroscopic images allows stereo fluoroscopy. The fluoroscopic images of 10 frames obtained by 10 viewpoints allow stereo fluoroscopy in nine directions. The doctor can obtain stereo fluoroscopy by selecting the most preferable direction among the nine directions. The doctor can also obtain stereo fluoroscopy while arbitrarily switching the nine directions.

In the biplane form as well, two fluoroscopic angles are set. However, there is no limitation on angle differences, and hence it is possible to set two arbitrary fluoroscopic angles. In the biplane form, when the operator sets one fluoroscopic angle, the apparatus initially displays two candidate lines having a fluoroscopic angle difference of 90° at front and back positions (see FIG. 12). Typically, the apparatus sets two fluoroscopic angles having an angle difference of 90°. In the combined form, the apparatus repeats fluoroscopic angle setting procedures in the stereo fluoroscopy form and the biplane form. The two fluoroscopic angles set in the stereo fluoroscopy form and the two fluoroscopic angles set in the biplane form commonly include one set fluoroscopic angle (see FIG. 11).

FIG. 4 shows another simple fluoroscopy condition setting support window 131 based on the fluoroscopy condition setting support unit 121. In this case, no volume scan is required. The fluoroscopy condition setting support unit 121 superimposes a fluoroscopic line 201 indicating the first fluoroscopic angle and a fluoroscopic line 202 indicating the second fluoroscopic angle on a rotational orbit 200 of the X ray tube 101. A fluoroscopic line is a line segment connecting a viewpoint on the rotational orbit 200 from which X-rays are applied to the center of the detector. The operator drags the fluoroscopic lines 201 and 202 to rotate them to arbitrary angles with a pointer 203, and determines the positions of the fluoroscopic lines at desired fluoroscopic angles. The same window displays a numerical value display field 204 for the first fluoroscopic angle, a numerical value display field 205 for the second fluoroscopic angle, a numerical value display field 206 for a fluoroscopic angle difference between them, a time difference display field 207 for the value obtained by dividing the fluoroscopic angle difference by a rotational angular velocity, and an ON/OFF setting field 208 for stereoscopic vision. These values are associated with rotating operation for the fluoroscopic lines 201 and 202. Numerically inputting the first and second fluoroscopic angles will rotate the fluoroscopic lines 201 and 202 to the input values. When stereoscopic vision (stereo fluoroscopy) is set ON, the input range of the second fluoroscopic angle is limited relative to the first fluoroscopic angle such that the angle difference between the first and second fluoroscopic angles falls with the range of 5° to 10°. When stereoscopic vision (stereo fluoroscopy) is set OFF, the fluoroscopy condition setting support unit 121 releases the limitation on the angle difference between the first and second fluoroscopic angles.

FIG. 5 shows still another simple fluoroscopy condition setting support window based on the fluoroscopy condition setting support unit 121. In this case, the fluoroscopy condition setting support unit 121 displays all or some of a plurality of projection images 211 acquired by volume scans at different view angles in thumbnails. When the doctor designates one of the plurality of projection images 211 which he/she determines as the fluoroscopic image 211 allowing to easily see a surgery target region, the fluoroscopy condition setting support unit 121 superimposes viewpoint marks 213 corresponding to the designated fluoroscopic image 211 on a rotational orbit model 212 of the X-ray tube 101. The fluoroscopy condition setting support unit 121 displays the designated fluoroscopic image 211 upon slightly enlarging it or with high luminance. When the doctor drags the viewpoint marks 213 to move them on the rotational orbit model 212 to arbitrary angles with the pointer 203, the fluoroscopy condition setting support unit 121 displays the corresponding fluoroscopic image 211 upon slightly enlarging it or with high luminance. The doctor determines desired fluoroscopic angles while checking the projection image.

Figure 6:
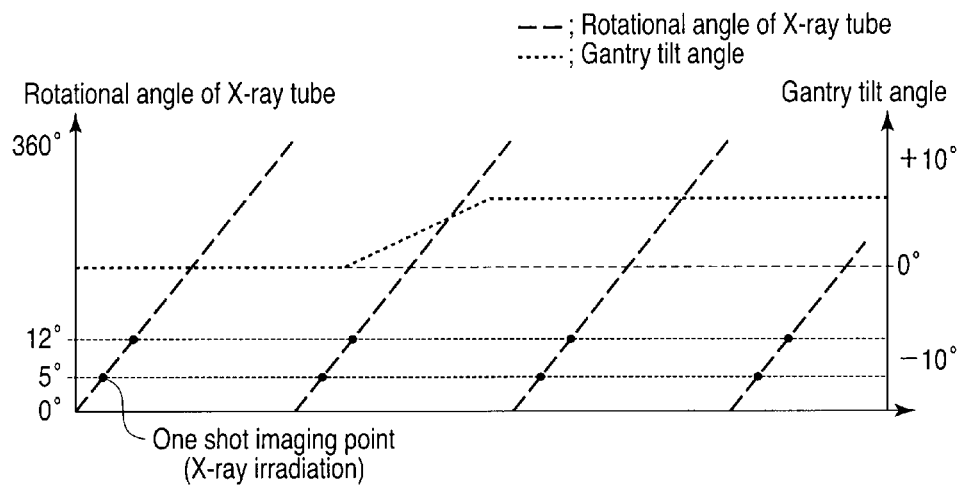
FIG. 6 is a graph showing the relationship between the rotation of an X-ray tube and the fluoroscopic angle in this embodiment.
Figure 8:
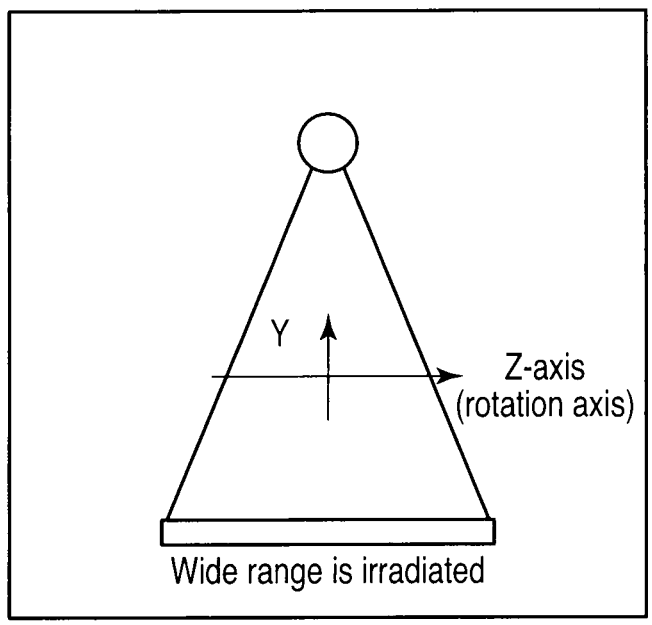
FIG. 8 is a view showing the irradiation range at the time of fluoroscopy in step S15 in FIG. 3.
Figure 9:
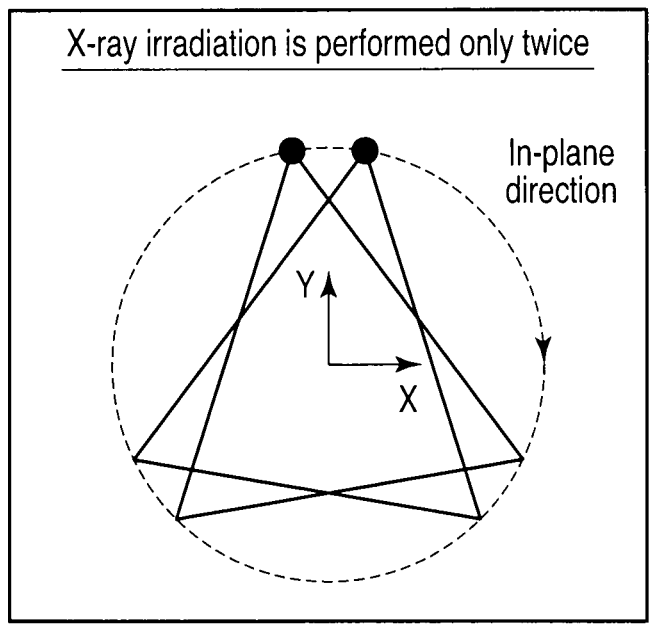
FIG. 9 is a view showing the fluoroscopy position in step S15 in FIG. 3.
Figure 13:
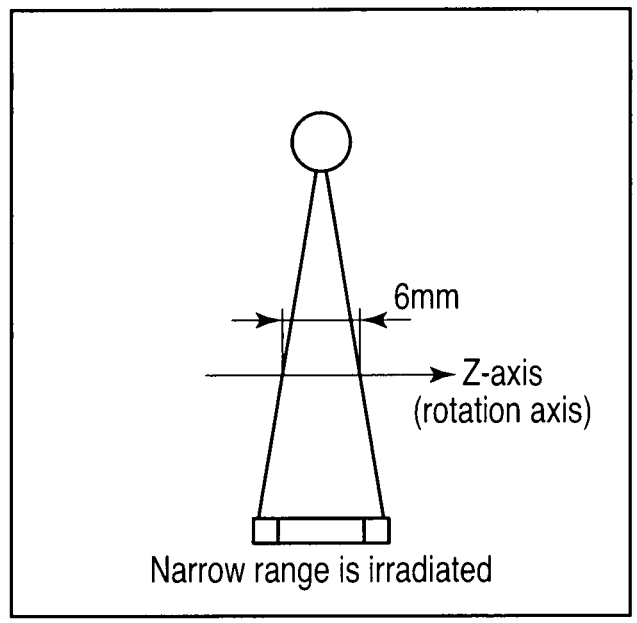
FIG. 13 is a view showing the field angle at the time of CT fluoroscopy in the use of a conventional three-array detector.
Figure 14:
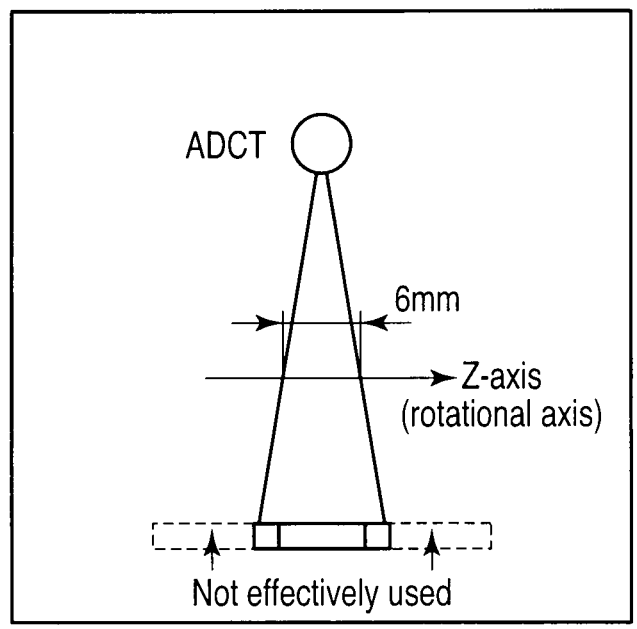
FIG. 14 is a view showing the field angle at the time of CT fluoroscopy in the use of a conventional multi-array detector.

When the doctor sets fluoroscopic angles in the above manner, the apparatus moves the gantry 100 or the top 138 to the fluoroscopy position (S13). Upon completing the above preparation, the doctor issues an instruction to start fluoroscopy (S14). The apparatus continuously rotates the annular frame 102 together with the X-ray tube 101 and the X-ray detector 103. The annular frame 102 keeps rotating until the doctor issues an instruction to finish fluoroscopy (S19). When the doctor turns on the footswitch 119 during continuous rotation of the annular frame 102, the X ray tube 101 irradiates the object with pulse X-rays two or three times per rotation during the ON period of the footswitch 119 (S15). As shown in FIGS. 6 and 9, an irradiation point is a viewpoint corresponding to a set fluoroscopic angle. As shown in FIG. 8, the X-ray tube 101 irradiates the object with X-rays with the maximum fan angle and the maximum cone angle in accordance with the sensitivity area of the X-ray detector 103 so as to irradiate the entire sensitivity area in which the detection elements of the X-ray detector 103 are arranged.

The projection image corresponding to the first fluoroscopic angle is displayed as, for example, a right-eye image, on a window (right-eye window) assigned in advance to the stereo monitor 117 or the eyeglass type stereo monitor 118. The projection image corresponding to the second fluoroscopic angle is displayed in real time as, for example, a left-eye image, on a window (left-eye window) assigned in advance to the stereo monitor 117 or the eyeglass type stereo monitor 118. Right- and left-eye images each are displayed as a moving image at a frame rate equal to the reciprocal of the time taken for one rotation.

When the biplane form is selected, a projection image corresponding to the first fluoroscopic angle is displayed on one window of the stereo monitor 117 or eyeglass type stereo monitor 118, and a projection image corresponding the second fluoroscopic angle is displayed on the other window or the monitor 116. When the combined form is selected, left- and right-eye projection images are displayed on the respective windows of the stereo monitor 117 or eyeglass type stereo monitor 118, and a projection image having a fluoroscopic angle difference of 90° is displayed on the monitor 116.

Figure 7:
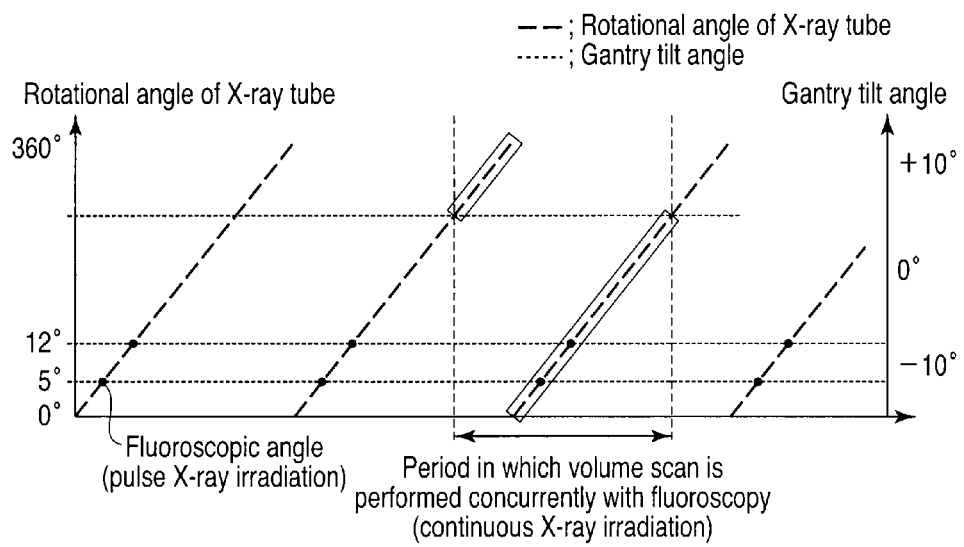
FIG. 7 is a graph showing the relationship between fluoroscopy and a scan in this embodiment.

When the doctor inputs an instruction to tilt the gantry during fluoroscopy, the apparatus tilts the gantry 100 in the designated direction while continuing fluoroscopy, as shown in FIG. 6. When the doctor inputs an instruction to perform a volume scan during fluoroscopy (S16), the apparatus continuously irradiates the object with X-rays, with the maximum fan angle and the maximum cone angle being kept unchanged, only during the interval between the start of the volume scan and the end of one rotation or a designated number of rotations, as shown in FIG. 7. The reconstruction device 114 reconstructs volume data based on the projection data acquired by the volume scan. The three-dimensional image processing unit 128 generates a pseudo three-dimensional image from the volume data. The monitor 116 then displays the image. Along with this operation, the apparatus displays projection data at viewpoints corresponding to the first and second fluoroscopic angles as projection images and continues fluoroscopy. In practice, since reconstruction processing for volume data and three-dimensional image processing require a longer processing time than projection image display (fluoroscopy), the display operation is not real-time operation.

When the doctor issues an instruction to change (re-set) the fluoroscopy position during fluoroscopy as in step S12 (S17), the flow returns to step S13 to move the gantry 100 to the position.

The apparatus repeats the above fluoroscopy operation until the achievement of the object, i.e., the end of catheterization (S18). Thereafter, the apparatus terminates the fluoroscopy (S19). Finally, the apparatus executes a volume scan. The reconstruction device 114 then reconstructs volume data based on the projection data acquired by the above operation. The three-dimensional image processing unit 128 generates a pseudo three-dimensional image from the volume data. The monitor 116 displays the generated image. This allows the doctor to check the catheterization result (S20).

The following is the operation based on the assumption of specific treatment.
(Liver Cancer TAE (Transcatheter Hepatic Arterial Embolization)

(1) The doctor captures a simple CT image, and then determines a range for fluoroscopy by ADCT Volume Scan (16 cm) including a wide field-of-view area detector.

(2) The doctor moves the catheter to the SMA (Superior Mesenteric Artery) by using the plane fluoroscopy function, and then captures a CTAP (CT during Arterial Portography) image with Volume Scan.

(3) The doctor moves the catheter to the common hepatic artery with the aid of plane fluoroscopy, and then captures a CTA image with Volume Scan.

(4) The doctor generates a three-dimensional image of blood vessels by CTA, and then identifies the feeding vessel of the tumor.

(5) The doctor manipulates and moves the microcatheter to the feeding vessel of the tumor while checking the three-dimensional image.

(6) The doctor checks how the tumor is contrast-enhanced by CTA.

(7) The doctor injects an embolus to the tumor while checking it with the aid of plane fluoroscopy.

(8) The doctor determines by CTA that the embolus is fully applied to the tumor.

In step (5) described above, this apparatus displays a position where the doctor can recognize a blood vessel branch portion from the generated three-dimensional image. The gantry is rotated and tilted to the position (manually or automatically), and the doctor checks it with the aid of plane fluoroscopy. The apparatus performs stereoscopic imaging to implement stereoscopic vision while rotating the gantry. The doctor operates the catheter and guides it to a proper blood vessel while checking the actual state of the microcatheter and a blood vessel running state in a three-dimensional CTA image. General triple-slice fluoroscopy cannot be effectively used with an insufficient range.

This embodiment can implement stereoscopic vision with only two times of X-ray irradiation per rotation, and hence allows smooth operation with low X-ray exposure. The doctor repeats the operation while changing the display position, as needed (in this case, the three-dimensional display mode based on CTA operates in association with the operation of the doctor).

(Needle Biopsy (Lung Fields))

(1) The doctor determines a range in which fluoroscopy is performed by ADCT Volume Scan (16 cm) upon capturing a simple CT image.

(2) The doctor generates a three-dimensional image and makes an examination on a guide which guides a needle to the tumor without damaging the bronchi and blood vessels.

(3) The apparatus calculates a display angle at which the doctor can easily recognize main blood vessels and bronchi along the guide.

(4) The apparatus rotates and tilts the gantry in accordance with the angle, and the doctor checks the resultant state with the aid of plane fluoroscopy.

(5) The doctor performs stereoscopic imaging while rotating the gantry, obtains stereoscopic vision, and moves the biopsy needle to the target tumor while checking the positions of blood vessels and bronchi around the needle.

(6) The doctor repeats this operation while changing the display position, as needed.

As has been described above, according to this embodiment, it is possible to obtain a three-dimensional CT fluoroscopic image in a wide range with the minimum X-ray exposure utilizing the advantages of ADCT. In addition, it can be expected to improve accuracy and shorten the surgery time by fusing puncture or catheterization with a three-dimensional volume image. Furthermore, it is possible to implement the X-ray computed tomography apparatus at a low cost without performing reconstruction and MPR for several hundred images in real time.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus, comprising:
    a single X-ray tube;
    an X-ray detector including a plurality of X-ray detection elements arrayed two-dimensionally;
    a rotating mechanism that supports the single X-ray tube and the X-ray detector so as to allow the single X-ray tube and the X-ray detector to rotate around an object;
    a high voltage generator that generates a high voltage to be applied to the single X-ray tube so as to make the single X-ray tube generate X-rays;
    a reconstruction processor that reconstructs multislice tomographic data or volume data based on an output from the X-ray detector;
    a setting supporter that sets respective angles of a pair of viewpoints on a rotational orbit of the single X-ray tube which corresponds to a binocular parallax;
    a projection image generator that generates a series of right-eye projection images corresponding to one of the pair of viewpoints and a series of left-eye projection images corresponding to the other of the pair of viewpoints based on an output from the X-ray detector during rotation of the single X-ray tube,
    an image display; and
    a fluoroscopy controller that controls the rotating mechanism, the high voltage generator, the X-ray detector, the projection image generator, and the image display to implement stereo fluoroscopy using the series of right-eye projection images and the series of left-eye projection images as a moving image on the image display in real time during rotation of the single X-ray tube, wherein the object is automatically irradiated with X-rays every time the single X-ray tube passes through the set angles set by the setting supporter.

2. The X-ray computed tomography apparatus according to claim 1, wherein the pair of viewpoints has an angular difference within a range of 5° to 10°.

3. The X-ray computed tomography apparatus according to claim 1, wherein positions of the pair of viewpoints are changed during rotation of the single X-ray tube.

4. The X-ray computed tomography apparatus according to claim 1, further comprising a user interface that receives an operator instruction during rotation of the single X-ray tube, wherein a fluoroscopy scan operation of causing the single X-ray tube to apply X-rays every time the single X-ray tube passes through the pair of viewpoints and a volume scan operation of causing the single X-ray tube to continuously apply X-rays are switched in accordance with the operator instruction.

5. The X-ray computed tomography apparatus according to claim 1, wherein the setting supporter generates a setting support window for setting the pair of viewpoints.

6. The X-ray computed tomography apparatus according to claim 5, wherein the setting support window includes the respective angles of the pair of viewpoints, an angle difference between the pair of viewpoints, and a time difference corresponding to the angle difference between the pair of viewpoints.

7. The X-ray computed tomography apparatus according to claim 6, wherein the setting support window includes a schematic view of a rotational orbit of the single X-ray tube and marks on the schematic view indicating the pair of viewpoints.

8. The X-ray computed tomography apparatus according to claim 1, wherein X-rays are applied from one of the pair of viewpoints and the other viewpoint shifted therefrom by 90°.

9. The X-ray computed tomography apparatus according to claim 1, further comprising:
    a tilt mechanism that tilts a rotation axis of the single X-ray tube and the X-ray detector; and
    a user interface that receives an operator instruction, wherein
    the fluoroscopy controller controls the tilt mechanism to tilt the rotation axis in accordance with the operator instruction concurrently with a continuous rotation, generation of the X-rays, and display of the projection image.

10. The X-ray computed tomography apparatus according to claim 1, further comprising a user interface that receives an operator instruction, wherein the fluoroscopy controller controls the high voltage generator to displace the pair of viewpoints on the rotational orbit of the single X-ray tube in accordance with the operator instruction concurrently with a continuous rotation, generation of the X-rays, and display of the projection image.

11. The X-ray computed tomography apparatus according to claim 1, further comprising a three-dimensional image processor that generates two-dimensional images with the pair of viewpoints as viewpoints from the reconstructed multislice tomographic data or volume data.

12. The X-ray computed tomography apparatus according to claim 1, wherein the single X-ray tube is a single-source X-ray tube and the object is irradiated at each of the pair of viewpoints using the single-source X-ray tube.

13. The X-ray computed tomography apparatus according to claim 1, wherein the fluoroscopy controller causes the object to be irradiated only at the set angles of the pair of viewpoints during a plurality of rotations of the single X-ray tube and the X-ray detector around the object.

14. An X-ray computed tomography apparatus, comprising:
a single X-ray tube;
an X-ray detector including a plurality of X-ray detection elements arrayed two-dimensionally;
a rotating mechanism configured to support the single X-ray tube and the X-ray detector so as to allow the single X-ray tube and the X-ray detector to rotate around an object;
a high voltage generating unit configured to generate a high voltage to be applied to the single X-ray tube so as to make the single X-ray tube generate X-rays;
a reconstruction processing unit configured to reconstruct multislice tomographic data or volume data based on an output from the X-ray detector;
a projection image generating unit configured to generate projection images used for stereo fluoroscopy based on output from the X-ray detector;
an image display;
a setting support unit configured to set respective angles of not less than three viewpoints; and
a fluoroscopy control unit configured to control the rotating mechanism, the high voltage generating unit, the X-ray detector, the projection image generating unit, and the image display to implement the stereo fluoroscopy, wherein the single X-ray tube continuously rotates together with the X-ray detector, the object is irradiated with X-rays every time the single X-ray tube passes through the set angles of the not less than three viewpoints on a rotational orbit, the set angles of not less than three viewpoints are shifted from each other by an angle corresponding to a binocular parallax, the projection image generating unit generates a series of not less than three projection images corresponding to the not less than three viewpoints based on an output from the X-ray detector during rotation of the single X-ray tube, and the image display displays, as a moving image, a series of two projection images corresponding to two adjacent viewpoints selected from the respective angles of the not less than three viewpoints in accordance with an operator instruction during rotation of the single X-ray tube,
wherein the object is irradiated at each of the respective angles of the not less than three viewpoints at corresponding times using the single X-ray tube to obtain projection images used for the stereo fluoroscopy.

15. The X-ray computed tomography apparatus according to claim 14, wherein the setting support unit causes a setting support window to be displayed and to set the respective angles of the not less than three viewpoints based on operator input into the setting support window.

* * * * *